US009056081B2

(12) United States Patent
Schachner et al.

(10) Patent No.: US 9,056,081 B2
(45) Date of Patent: Jun. 16, 2015

(54) COMPOSITIONS FOR TREATING PSEUDOMONAS INFECTION (75) Inventors: Melita Schachner, Hamburg (DE); Heike Gustke, Hamburg (DE); Udo Schumacher, Wentorf (DE); Karl-Erich Jäger, Mülheim an der Ruhr (DE)

(73) Assignees: Universitätsklinikum Hamburg-Eppendorf (DE); Heinrich-Heine-Universität Düsseldorf (DE)

( * ) Notice: Subject to any disclaimer, the term of this patent is extended or adjusted under 35 U.S.C. 154(b) by 46 days.

(21) Appl. No.: 13/319,262

(22) PCT Filed: May 10, 2010

(86) PCT No.: PCT/EP2010/002857
§ 371 (c)(1),
(2), (4) Date: Apr. 30, 2012

(87) PCT Pub. No.: WO2010/127877
PCT Pub. Date: Nov. 11, 2010

(65) Prior Publication Data
US 2012/0283173 A1     Nov. 8, 2012

(30) Foreign Application Priority Data
May 8, 2009  (EP) .................................... 09159764

(51) Int. Cl.
*A61K 38/17*    (2006.01)
*A61K 9/00*     (2006.01)

(52) U.S. Cl.
CPC .............. *A61K 38/177* (2013.01); *A61K 9/008* (2013.01)

(58) Field of Classification Search
None
See application file for complete search history.

(56) References Cited

U.S. PATENT DOCUMENTS

| 6,080,724 A | 6/2000 | Chassaing |
| 2003/0100508 A1 | 5/2003 | Simon et al. |
| 2003/0175894 A1* | 9/2003 | Wei et al. ..................... 435/69.5 |

FOREIGN PATENT DOCUMENTS

| WO | WO-00/50447 A1 | 8/2000 |
| WO | WO-2010/127877 A1 | 11/2010 |

OTHER PUBLICATIONS

Simon-Haldi M,, et al, "Identification of a peptide mimic of the L2/HNK-1 carbohydrate epitope," J Neurochem. Dec. 2002;83(6):1380-8.*
"European Application Serial No. 09159764.1, European Search Report mailed Oct. 30, 2009", 5 pgs.
"International Application Serial No. PCT/EP2010/002857, Written Opinion mailed Aug. 6, 2010", 4 pgs.
"International Application Serial No. PCT/EP2010/002857, International Preliminary Report on Patentability dated Nov. 9, 2011", 5 pgs.
Abo. T. et al., "A Differentiation Antigen of Human NK and K Cells Identified by a Monoclonal Antibody (HNK-1)", *The Journal of Immmunology*, 127(3), (1981), 1024-1029.
Adam, E. C., et al., "*Pseudomonas aeruginosa* II Lectin Stops Human Ciliary Beating: Therapeutic Implications of Fucose", *Am. J. Respir. Crit. Care Med.*, 155, (1997), 2102-2104.
Altschul, S. F., et al., "Basic Local Alignment Search Tool", *J. Mol. Biol.*, 215, (1990), 403-410.
Altschul, S. F., "Gapped Blast and PSI-Blast: A New Generation of Protein Database Search Programs", *Nucleic Acids Research*, 25(17), (1997), 3389-3402.
Andersson, L. et al., "Large-Scale Synthesis of Peptides", *Biopolymers (Peptide Science)*, 55, (2000), 227-250.
Chen, Y., et al,, "Transdermal protein delivery by a coadrninistered peptide identified via phage display", *Nature Biotechnology*, 24(4), (2006), 455-460.
Gilboa-Garber, N., "[32]. *Psoudemonas aeruginosa* Lectins", *Methods Enzymol.*, 83, (1982), 378-396.
Gilboa-Garber, N., et al., "Microbial lectin cofunction with lytic activities as a model fora general basic lectin role", *FEMS Microbiology Reviews*, 63, (1989), 211-222.
Henikoff, S., et al., "Amino acid substitution matrices from protein blocks", *Proc. Natl. Acad. Sci. USA*, 89(22), (Nov. 15, 1989), 10915-10919.
Ilyas, A. A., et al., "IgM in a human neuropathy related to paraproteinema binds to a carbohydrate determinant in the myelin-associated glycoprotein and to a ganglioside", *Proc. Natl. Acad. Sci. USA*, 81, (1984), 1225-1229.
Kruse, J., et al., "Neural cell adhesion molecules and myelin-associated glycoprotein share a common carbohydrate moiety recognized by monoclonal antibodies L2 and HNK-1". Nature, 311. (1984), 153-155.
Merrifield, R. B. "Solid Phase Peptide Synthesis. I. The Synthesis of a Tetrapeptide", *The Journal of the American Chemical Society*, 85(41), (Jul. 20, 1963), 2149-2154.

(Continued)

*Primary Examiner* — Thomas S Heard
(74) *Attorney, Agent, or Firm* — Schwegman Lundberg & Woessner, P.A.

(57) ABSTRACT

The invention relates to a HNK-I mimetic peptide or a polypeptide comprising such HNK-I mimetic peptide for treating or preventing a *Pseudomonas* infection, in particular an infection with *Pseudomonas aeruginosa*. The invention further relates to the use of a HNK-I mimetic peptide or a polypeptide comprising such HNK-I mimetic peptide for the preparation of a pharmaceutical composition for treating or preventing a *Pseudomonas* infection. The invention also relates to a pharmaceutical composition comprising a HNK-I mimetic peptide or a polypeptide comprising such HNK-I mimetic peptide, wherein the composition is for treating or preventing a *Pseudomonas* infection.

7 Claims, 4 Drawing Sheets

(56) References Cited

OTHER PUBLICATIONS

Noronha, A. B., et al., "Molecular Specificity of L2 Monoclonal Antibodies that Bind to Carbohydrate Determinants of Neural Cell Adhesion Molecules and their Resemblance to other Monoclonal Antibodies Recogniizing the Myelin-Associated Glycoprotein", *Brain Research*, 385, (1986), 237-244.

Pearson, W. R., "[15] Effective Protein Sequence Comparison", *Methods in Enzymology*, 266, (1996), 227-258.

Quarles, R. H., et al., "12. Myelin-Associated Glycoprotein: Structure-Function Relationships and Involvement in Neurological Diseases", *In: Biology and Chemistry*, (1992), 413-448.

Schachner, M., "Families of neural adhesion molecules", *Ciba Foundation Symposium*, 145, (1989), 156-172.

Schachner, M., et al., "Glycans and the modulation of neural-recognition molecule function", *Trends Neurosci.*, 18, (1995), 183-191.

Steuer, M. K., et al., "Hemmung der bakteriellen Adhasion durch Lektinblockade bei durch *Pseudomonas aeruginosa* induzierter Otitis externa im Vergleich zuriekalen Therapie mit Antibiotika" ["Inhibition of Lectin-Mediated Bacterial Adhesion by Receptor-Blocking Carbohydrates in Patients with *Pseudomonas-aeruginosa*-Induced Otitis externa: A Prospective Phase II Study"], (w/ English Abstract), *Otorhinolaryngol Nova*, 3, (1993), 19-25.

Von Bismarck, S., et al., "Mediane Halszysten im Kindesalter: fruhzeitige Operation senkt die Komplikationsrate", *Klin. Padiatr.*, 213, (2001), 295-298.

Winzer, K. et al., "The Pseudomonas aeruginosa Lectins PA-IL and PA-IIL Are Controlled by Quorum Sensing and RpoS", *Journal of Bacteriology*, 182(22), (2000), 6401-6411.

"International Application Serial No. PCT/EP2010/002857, International Search Report mailed Aug. 6, 2010", 3 pgs.

\* cited by examiner

SEQUENCE LISTING

<160> NUMBER OF SEQ ID NOS: 21

<210> SEQ ID NO 1
<211> LENGTH: 8
<212> TYPE: PRT
<213> ORGANISM: Artificial
<220> FEATURE:
<223> OTHER INFORMATION: synthetic peptide

<400> SEQUENCE: 1

Phe Leu His Thr Arg Leu Phe Val
1               5

<210> SEQ ID NO 2
<211> LENGTH: 15
<212> TYPE: PRT
<213> ORGANISM: Artificial
<220> FEATURE:
<223> OTHER INFORMATION: synthetic peptide

<400> SEQUENCE: 2

Phe Leu His Thr Arg Leu Phe Val Ser Asp Trp Tyr His Thr Pro
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic peptide

<400> SEQUENCE: 3

Thr Phe Thr Arg Val Val Thr Asp Val Tyr Arg Gly Arg Leu Ser
1               5                   10                  15

```
<210> SEQ ID NO 4
<211> LENGTH: 15
<212> TYPE: PRT
<213> ORGANISM: Artificial
<220> FEATURE:
<223> OTHER INFORMATION: synthetic peptide

<400> SEQUENCE: 4

Phe Leu His Thr Arg Leu Phe Val Ser Asp Trp Tyr Asn Thr Pro
1               5                   10                  15

<210> SEQ ID NO 5
<211> LENGTH: 15
<212> TYPE: PRT
<213> ORGANISM: Artificial
<220> FEATURE:
<223> OTHER INFORMATION: synthetic peptide

<400> SEQUENCE: 5

Phe Leu His Thr Arg Leu Leu Phe Arg Ile Val Ser Tyr Ser Gly
1               5                   10                  15

<210> SEQ ID NO 6
<211> LENGTH: 15
<212> TYPE: PRT
<213> ORGANISM: Artificial
<220> FEATURE:
<223> OTHER INFORMATION: synthetic peptide

<400> SEQUENCE: 6

Phe Leu His Thr Arg Leu Leu Phe Arg Asn Gly Ile Ile Leu Arg
1               5                   10                  15

<210> SEQ ID NO 7
<211> LENGTH: 15
<212> TYPE: PRT
<213> ORGANISM: Artificial
<220> FEATURE:
<223> OTHER INFORMATION: synthetic peptide

<400> SEQUENCE: 7

Phe Leu His Thr Arg Leu Phe Val Ser Asp Gly Ile Asn Ser Gly
1               5                   10                  15

<210> SEQ ID NO 8
<211> LENGTH: 15
<212> TYPE: PRT
<213> ORGANISM: Artificial
<220> FEATURE:
<223> OTHER INFORMATION: synthetic peptide

<400> SEQUENCE: 8

Phe Leu His Thr Arg Leu Phe Val Ser Asp Trp Tyr His Thr Pro
1               5                   10                  15

<210> SEQ ID NO 9
<211> LENGTH: 15
<212> TYPE: PRT
<213> ORGANISM: Artificial
<220> FEATURE:
<223> OTHER INFORMATION: synthetic peptide

<400> SEQUENCE: 9

Thr Arg Leu Phe Arg Val Pro Val Phe Arg Leu Gly Asp Phe Trp
1               5                   10                  15
```

```
<210> SEQ ID NO 10
<211> LENGTH: 15
<212> TYPE: PRT
<213> ORGANISM: Artificial
<220> FEATURE:
<223> OTHER INFORMATION: synthetic peptide

<400> SEQUENCE: 10

Thr Arg Leu Phe Arg Phe Leu Ser Ser Val Trp Gly Leu Leu Ala
1               5                   10                  15

<210> SEQ ID NO 11
<211> LENGTH: 15
<212> TYPE: PRT
<213> ORGANISM: Artificial
<220> FEATURE:
<223> OTHER INFORMATION: synthetic peptide

<400> SEQUENCE: 11

Thr Arg Leu Phe Arg Val Pro Val Leu Pro Ser Gly Val Thr Ser
1               5                   10                  15

<210> SEQ ID NO 12
<211> LENGTH: 16
<212> TYPE: PRT
<213> ORGANISM: Artificial
<220> FEATURE:
<223> OTHER INFORMATION: synthetic peptide

<400> SEQUENCE: 12

Ser Leu Ala Pro Tyr Ser Leu Arg Ile Phe Val Leu Phe Gly Gly Ala
1               5                   10                  15

<210> SEQ ID NO 13
<211> LENGTH: 17
<212> TYPE: PRT
<213> ORGANISM: Artificial
<220> FEATURE:
<223> OTHER INFORMATION: synthetic peptide

<400> SEQUENCE: 13

Ser Leu Ala Arg Ser Phe His Ala Tyr Phe Arg His Thr Leu Val Gly
1               5                   10                  15

Pro

<210> SEQ ID NO 14
<211> LENGTH: 12
<212> TYPE: PRT
<213> ORGANISM: Artificial
<220> FEATURE:
<223> OTHER INFORMATION: synthetic peptide

<400> SEQUENCE: 14

Thr Phe Lys Leu Ser Glu Thr Thr Leu Glu Tyr Tyr
1               5                   10

<210> SEQ ID NO 15
<211> LENGTH: 12
<212> TYPE: PRT
<213> ORGANISM: Artificial
<220> FEATURE:
<223> OTHER INFORMATION: synthetic peptide

<400> SEQUENCE: 15

Thr Phe Gln Leu Ser Thr Arg Thr Leu Pro Phe Ser
1               5                   10
```

```
<210> SEQ ID NO 16
<211> LENGTH: 7
<212> TYPE: PRT
<213> ORGANISM: Artificial
<220> FEATURE:
<223> OTHER INFORMATION: synthetic peptide

<400> SEQUENCE: 16

Leu Ser Glu Thr Thr Leu Leu
1               5

<210> SEQ ID NO 17
<211> LENGTH: 6
<212> TYPE: PRT
<213> ORGANISM: Artificial
<220> FEATURE:
<223> OTHER INFORMATION: synthetic peptide

<400> SEQUENCE: 17

Arg Thr Leu Pro Phe Ser
1               5

<210> SEQ ID NO 18
<211> LENGTH: 8
<212> TYPE: PRT
<213> ORGANISM: Artificial
<220> FEATURE:
<223> OTHER INFORMATION: synthetic peptide

<400> SEQUENCE: 18

Thr Val Phe His Phe Arg Leu Leu
1               5

<210> SEQ ID NO 19
<211> LENGTH: 13
<212> TYPE: PRT
<213> ORGANISM: Artificial
<220> FEATURE:
<223> OTHER INFORMATION: synthetic peptide

<400> SEQUENCE: 19

Ser Ala Cys Ser Arg Leu Asn Tyr Leu His Cys Lys Lys
1               5                   10

<210> SEQ ID NO 20
<211> LENGTH: 13
<212> TYPE: PRT
<213> ORGANISM: Artificial
<220> FEATURE:
<223> OTHER INFORMATION: synthetic peptide

<400> SEQUENCE: 20

Ser Ala Cys Asn His Leu Leu Arg Ser Tyr Cys Lys Lys
1               5                   10

<210> SEQ ID NO 21
<211> LENGTH: 6
<212> TYPE: PRT
<213> ORGANISM: Artificial
<220> FEATURE:
<223> OTHER INFORMATION: synthetic consensus sequence

<400> SEQUENCE: 21

Phe Leu His Thr Arg Leu
1               5
```

COMPOSITIONS FOR TREATING PSEUDOMONAS INFECTION

PRIORITY CLAIM AND RELATED APPLICATIONS

This application is a nationalization under 35 U.S.C. 371 of PCT/EP2010/002857, filed May 10, 2010 and published as WO 2010/127877 A1 on Nov. 11, 2010, which claimed priority under 35 U.S.C. 119 to European Patent Application No. 09159764.1, filed May 8, 2009; which applications and publication are incorporated herein by reference in their entirety.

The invention relates to a HNK-1 mimetic peptide or a polypeptide comprising such HNK-1 mimetic peptide for treating or preventing a *Pseudomonas* infection, in particular an infection with *Pseudomonas aeruginosa*. The invention further relates to the use of a HNK-1 mimetic peptide or a polypeptide comprising such HNK-1 mimetic peptide for the preparation of a pharmaceutical composition for treating or preventing a *Pseudomonas* infection. The invention also relates to a pharmaceutical composition comprising a HNK-1 mimetic peptide or a polypeptide comprising such HNK-1 mimetic peptide, wherein the composition is for treating or preventing a *Pseudomonas* infection.

BACKGROUND OF THE INVENTION

*Pseudomonas aeruginosa*, an opportunistic pathogen, is ubiquitously present in the human environment. While it generally does not affect healthy subjects, it is able to cause severe respiratory tract infections or even septicaemia in susceptible individuals such as cystic fibrosis patients or cancer patients receiving chemotherapy. *Pseudomonas aeruginosa* produces two carbohydrate binding lectins, namely PA-IL and PA-IIL (Gilboa-Garber (1982) Methods Enzymol. 83:378-3), which bind to the glycocalyx including that of the airway cilia and thus facilitate airway infection (Gilboa-Garber and Garber (1989) FEMS Microbiol Rev. 5:211-221; Adam et al. (1997) Am J Respir Crit Care Med. 155:2102-2104). Both lectins contribute to adhesion by binding to cilia and are regulated by quorum sensing (Winzer et al. (2000) J Bacteriol. 182:6401-6411), a cell-cell communication mechanism used to monitor population density and coordinate gene regulation showing the importance of these pathogenicity factors.

As the two lectins play an important role in the interaction of the bacterium with human cells, the design of potent inhibitors of *Pseudomonas aeruginosa* lectins may have considerable implications for the generation of novel therapeutic agents urgently needed to fight *Pseudomonas aeruginosa* infections, as clinical relevant *Pseudomonas* strains are already resistant against a considerable number of antibiotics. It has been shown in the prior art that sugar solutions can block the lectin-sugar interaction in the clinical situation: monosaccharides specific for the two lectins were able to cure the *Pseudomonas aeruginosa* infection in the auditory canal (Steuer et al. (1993) Otorhinolaryngol Nova. 3:19-25) and in the airways (von Bismarck et al. (2001) Klin Padiatr. 213: 285-287). PA-IL has a high specificity for galactose, whereas PA-IIL, which is located in the bacterial outer membrane, exhibits a high specificity for L-fucose and its derivatives. However, these sugars have been shown to bind the lectin with low affinity and are, moreover, subject to rapid degradation which render them undesirable from a clinical viewpoint.

Accordingly, there is a need for means and methods of interfering with the binding of lectins of *Pseudomonas aeruginosa* to the glycocalyx of mammalian cells using inhibitory compounds which have improved affinity and stability characteristics. It has been found in the course of the present invention that synthetic peptides, which mimic an epitope from the HNK-1 carbohydrate, effectively inhibit *Pseudomonas* lectins. These peptides are referred to in the following as HNK-1 mimetic peptides or HNK-1 glycomimetics. The peptides are highly suitable for therapeutic use due to their stability towards degradation, their specificity and affinity for their cognate receptors, and their availability by well-known peptide synthesis methods.

HNK-1 mimetic peptides have been extensively described in the prior art, for example in the international application WO 00/50447. In 1981, a monoclonal IgM antibody was isolated which was directed against a membrane antigen from a cultured human T cell line (Abo and Balch, (1981) J. Immunology 127:1024-1029). This antibody was shown to react with 10% of blood lymphocytes and to recognize an antigen specific to human natural killer (NK) and killer (K) cells, thus the name HNK-1. NK and K cells are specialized lymphocytes that serve important roles in the surveillance of tumors and virus-infected cells. In the same study, it was mentioned that the HNK-1 epitope was resistant to proteolysis, suggesting that the epitope was of non-proteinaceous nature. It was later shown that the antigen is a carbohydrate (Kruse et al, (1984) Nature 311:153-155).

The HNK-1 carbohydrate is a trisaccharide consisting of a sulphated glucuronic acid, galactose and N-acetylglucosamine. It is predominantly found on glycolipids and glycoproteins from nervous tissue. Its pattern in both the central and peripheral nervous system is spatially and developmentally regulated. The HNK-1 carbohydrate is carried by many, but not all, neural recognition glycoproteins, and is involved in homophilic and heterophilic binding of these proteins (for a review, see Schachner and Martini (1995), Trends Neurosci. 18:183-191). Of particular note is the association of the epitope with Schwann cells myelinating motor but not sensory axons, where it may be involved in the preferential reinnervation of muscle nerves by motor axons after lesion. Accordingly, it has been contemplated to use HNK-1 mimetic peptides for enhancing myelination and to modulate neural growth. In view of the results obtained in the course of the present invention, it has to be assumed that the HNK-1 carbohydrate is also expressed in inflamed and repairing airways where it would provide an ideal attachment ligand for the two lectins of *Pseudomonas aeruginosa*.

Figure 1:
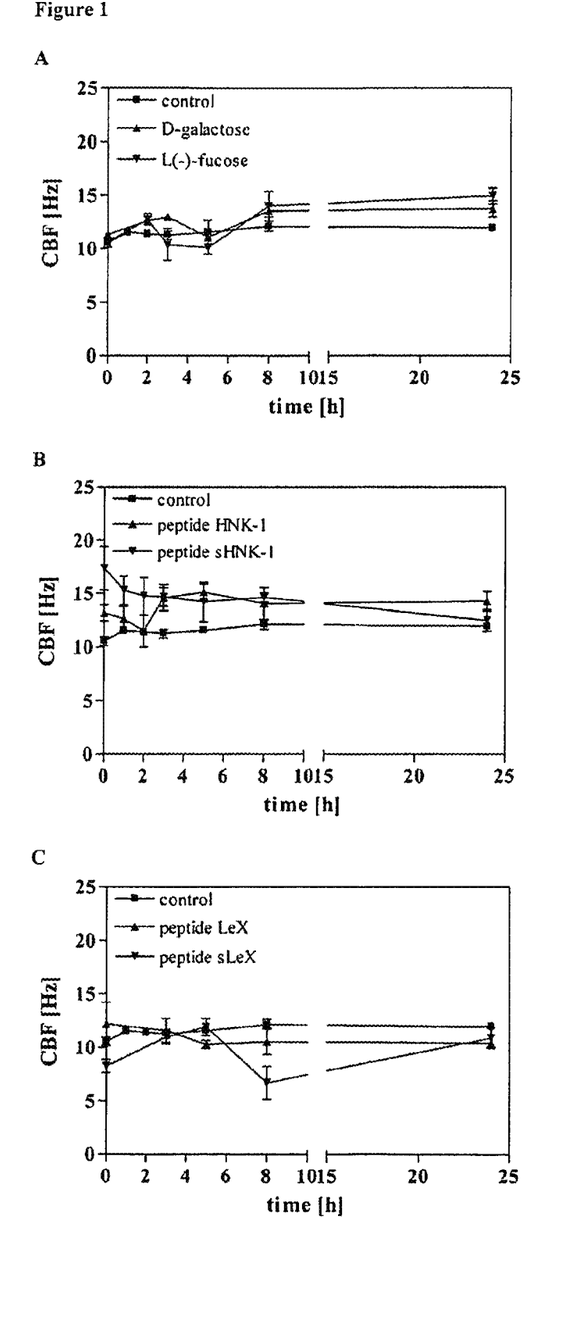
FIG. 1 shows the effects of specific monosaccharides and peptides on the ciliary beat frequency (CBF) over a 24 h period. The analysis showed that the monosaccharides D-galactose and L(−)-fucose (A) and the glycomimetic peptides pHNK-1 (B) and pLeX (C) had no effect on the CBF. The CBF of the negative control remained within the normal range (10-18 Hz). Values represent means±SEM.

As shown in the examples, HNK-1 mimetic peptides have been tested using a ciliary beat frequency (CBF) assay. In this type of assay, actively beating cilias are monitored by use of a microscope, and the effect of test compounds (such as HNK-1 mimetic peptides) on the reduction of the beat frequency that is induced by the *Pseudomonas* lectins PA-IL and PA-IIL is determined. It was found that the treatment of cilias with HNK-1 mimetic peptides alone (without co-incubation of lectins) did not change the ciliary beat frequency compared to controls, and the tested compounds did not influence cell morphology or survival (FIG. 1B).

The peptide pHNK-1 (SEQ ID NO:1) blocked the CBF-decreasing effect of PA-IL like D-galactose (FIGS. 2A and 2B). Interestingly, the peptide sHNK-1 (SEQ ID NO:18) having the same amino acid composition, but in a randomized order also reduced the CBF-decreasing effect of PA-IL (FIG. 2B). This peptide was originally included in the assay as a control only. However, it was found later that sHNK-1 is also a HNK-1 mimetic peptide. PA-IIL decreased the CBF within 24 hours and this effect could be reduced by co-incubation with 0.2 M L(−)-fucose (FIG. 3A). However, no inhibition could be achieved with the co-incubation of 0.2 M D-galactose and PA-IIL (FIG. 3A), indicating that PA-IIL has no overlapping specificity with PA-IL. Only pHNK-1 inhibited the CBF-decreasing effect of PA-IIL in the CBF analysis (FIG. 3B).

The peptide pHNK-1 inhibited the CBF-decreasing effect of both PA-IL ($IC_{50}$ 0.484 mM) and PA-IIL ($IC_{50}$ 0.968 mM) (FIG. 4A-D). In addition, pHNK-1 also caused an inhibition of lectin induced suppression of CBF after simultaneous application of both lectins (FIG. 4E). Hence, pHNK-1 is a better ligand for the lectins of *Pseudomonas aeruginosa* than their specific monosaccharides. It binds to both lectins which would result in the need of just a single blocking substance to be applied clinically. Galactose and fucose solutions are not stable and loose their inhibitory potency when stored at room temperature or at 4° C. dissolved in an aqueous solution (data not shown), hence making them impractical for therapeutic use, for example, by inhalation.

The present invention, according to a first aspect, relates to a HNK-1 mimetic peptide (or a polypeptide comprising such HNK-1 mimetic peptide) for treating or preventing a *Pseudomonas* infection. Preferably, the HNK-1 mimetic peptide is for treating or preventing a *Pseudomonas aeruginosa* infection. The HNK-1 mimetic peptide preferably comprises or consists of an amino acid sequence selected from the group of amino acid sequences depicted in SEQ ID NO:1 to SEQ ID NO:18 or an amino acid sequence having at least 80% identity thereto. More preferably, the HNK-1 mimetic peptide comprises or consists of the amino acid sequence depicted in SEQ ID NO:1 or an amino acid sequence having at least 80% identity thereto.

According to a second aspect, the invention relates to the use of a HNK-1 mimetic peptide (or a polypeptide comprising such HNK-1 mimetic peptide) for the preparation of a pharmaceutical composition for treating or preventing a *Pseudomonas* infection, in particular an infection with *Pseudomonas aeruginosa*. The HNK-1 mimetic peptide preferably comprises or consists of an amino acid sequence selected from the group of amino acid sequences depicted in SEQ ID NO:1 to SEQ ID NO:18 or an amino acid sequence having at least 80% identity thereto. More preferably, the HNK-1 mimetic peptide comprises or consists of the amino acid sequence depicted in SEQ ID NO:1 or an amino acid sequence having at least 80% identity thereto.

According to a third aspect, the invention relates to a pharmaceutical composition, which comprises a HNK-1 mimetic peptide (or a polypeptide comprising such HNK-1 mimetic peptide), for treating or preventing a *Pseudomonas* infection, in particular an infection with *Pseudomonas aeruginosa*. The HNK-1 mimetic peptide preferably comprises or consists of an amino acid sequence selected from the group of amino acid sequences depicted in SEQ ID NO:1 to SEQ ID NO:18 or an amino acid sequence having at least 80% identity thereto. More preferably, the HNK-1 mimetic peptide comprises or consists of the amino acid sequence depicted in SEQ ID NO:1 or an amino acid sequence having at least 80% identity thereto.

The invention also comprises embodiments in which more than one HNK-1 mimetic peptide is used for preparing the pharmaceutical composition of the invention. Therefore, the invention also pertains to pharmaceutical compositions comprising more than one HNK-1 mimetic peptide, for example, 2, 3, 4, 5, 6, 7, 8, 9 or 10 HNK-1 mimetic peptides (or polypeptides comprising such HNK-1 mimetic peptides).

As used in the context of the present invention, the term "peptide" refers to a series of 50 or less amino acid residues, preferably about 45, 40, 35, 30, 25, 20, 15, 10, 9, 8, 7, 6, 5 or less amino acid residues, which are connected one to the other by means of peptide or similar bonds between the alpha-amino group and carboxy group of contiguous amino acid residues. A HNK-1 mimetic peptide, as used in herein, is a peptide which mimics an epitope from the HNK-1 carbohydrate. A HNK-1 mimetic peptide therefore comprises or consists of an epitope which is recognized by an anti-HNK-1 antibody. Hence, a HNK-1 mimetic peptide reacts specifically and selectively with the paratope of an antibody produced by lymphoid cells, which have been contacted with HNK-1 as an immunogen. The peptide preferably reacts with the anti-HNK-1 antibody both in vitro and in vivo. According to the invention, the HNK-1 mimetic peptide preferably consists of 5 to 30 amino acid residues, more preferably 9 to 15, and most preferably of about 12 amino acid residues. The HNK-1 mimetic peptides may be linear or cyclic. For example, the peptides referred to in the present invention as SEQ ID NO:16 and 17 are cyclic peptides having a link between the N-terminal residue and the C-terminal residue.

HNK-1 mimetic peptides for use in the context of the invention have been extensively described in the prior art, for example in WO 00/50447. Methods for isolating HNK-1 mimetic peptides are known to the person of skill and, moreover, have been described in Example 1 of WO 00/50447. Furthermore, several anti-HNK-1 antibodies which can be used for isolating HNK-1 mimetic peptides have been described. For example, the anti-body described by Abo and Balch, (1981) J. Immunology 127:1024-1029, may be used for screening HNK-1 mimetic peptides. Further antibodies comprise monoclonal antibodies isolated from rat after immunization with a fraction that was enriched in plasma membrane include 334 (IgM), 336 (IgG), 349 (IgM), 344 (IgM), and 392 (IgM). Likewise, antibody L2-412 (IgG) can be used. The antibody L2-412 (IgG) was obtained by immunization with a membrane-derived glycoprotein fraction from mouse brain (Kruse J. et al, (1984), Nature 311, 153-155; Noronha, A. et al, (1986) Brain Res. 385, 237-244; Schachner M. et al, (1989) Schachner, M. Ciba Fdn. Symp. 145, 56-172). Another group of suitable monoclonal antibodies is disclosed in Ilyas, A. A. et al. (1984), Proc. Natl. Sci. USA 81, 1225-9 and Quarles, R. H. et al. (1992), Biology and Chemistry, 4413-4448.

Other HNK-1-specific antibodies can be obtained by standard techniques, such as those described in Antibodies: A Laboratory Manual, Howell and Lane, Coldspring Harbor Laboratory, 1988, for example, stimulating lymphoid cells with the HNK-1 carbohydrate as an immunogene. The anti-HNK-1 antibodies may be used in panning methods in which the antibody is coupled to a solid support and is subsequently used for binding assays with peptide libraries. For example, phage libraries may be screened for binding of a peptide to the antibody. Suitable methods for the identification of HNK-1 mimetic peptides are described, for example, in WO 00/50447.

The HNK-1 mimetic peptide according to the present invention preferably comprises or consists of an amino acid sequence selected from the group of amino acid sequences depicted in SEQ ID NO:1 to SEQ ID NO:18 or an amino acid sequence having at least 80%, preferably 90% identity thereto. It is preferred that the HNK-1 mimetic peptide comprises or consists of a sequence which is identical to one of the sequences provided in SEQ ID NO:1 to SEQ ID NO:18 or to a functional fragment thereof. The HNK-1 mimetic peptide may also comprise or consist of a sequence having at least 80%, preferably at least 90% identity to one of the sequences provided in SEQ ID NO:1 to SEQ ID NO:18. In the latter case the HNK-1 mimetic peptide comprises or consists of an amino acid sequence which differs from one of the sequences provided in SEQ ID NO:1 to SEQ ID NO:18 by one, two or three amino acid substitutions, preferably conservative amino acid substitutions. The HNK-1 mimetic peptides of the invention, for example, the peptide sequences provided in SEQ ID NO:1 to SEQ ID NO:18 or the sequences which are homologous thereto, may of course be part of a larger amino acid sequence, such as a polypeptide or protein sequence. The terms "polypeptide" and "protein" are used interchangeably herein to mean peptides having more than 50 amino acid residues, for example, 60, 70, 80, 90, 100, 150, 200, 250, 300, 400, 500, 600, 700, 800, 900, 1000 or more amino acids.

According to a particularly preferred embodiment of the invention, the HNK-1 mimetic peptide to be used in the pharmaceutical composition according to the invention is a peptide which comprises or consists of the sequence provided in SEQ ID NO:1 (designated pHNK-1) or an amino acid sequence having at least 80%, preferably at least 90% identity thereto or a peptide which differs from the peptide of SEQ ID NO:1 by one or two amino acid substitutions. It is of course also possible to use a larger molecule (such as a polypeptide or protein) which comprises the peptide of SEQ ID NO:1 or an amino acid sequence having at least 80%, preferably at least 90% identity thereto or a peptide which differs from the peptide of SEQ ID NO:1 by one or two amino acid substitutions.

In course of the invention, it has also been found that the therapeutic effect of the mimetic peptides on inhibition of Pseudomonas infection may be enhanced in several cases by exchanging certain L-amino acids by their respective D-amino acid counterparts. Accordingly, the present invention also contemplates derivatives of HNK-1 mimetic peptides, and in particular of the HNK-1 mimetic peptides provided herein as SEQ ID NOs:1-18, which differ from the original peptide molecule by the replacement of one or more L-amino acids by their respective D-amino acid counterpart.

The mimetic peptides disclosed herein are intended for preventing or treating a Pseudomonas infection in a mammalian subject, in particular a human subject. The peptides function by interference with the binding of Pseudomonas lectins to the glycostructures on mucosal surfaces. Preferably, the infection to be treated or prevented is caused by Pseudomonas aeruginosa, which is known to infect the pulmonary tract, the urinary tract, the external ear (otitis externa), and also injured skin, such as burns and wounds. It is the most frequent colonizer of medical devices, such as catheters, thereby causing cross infections in hospitals. If, after infection with Pseudomonas aeruginosa, colonisation occurs in critical body organs such as the lungs or kidneys, the results can be fatal. Diseases resulting from infection and colonisation with Pseudomonas aeruginosa, which can be treated by administering the HNK-1 mimetic peptides of the present invention, comprise pneumonia, meningitis, sepsis and similar conditions. A preferred field of use of the pharmaceutical compositions contemplated by the present invention is the prevention and treatment of respiratory tract or airway infections (e.g. tracheo-bronchitis) with Pseudomonas aeruginosa, in particular in patients with reduced immunity, such as patients with cystic fibrosis or cancer patients treated by chemotherapy.

A composition comprising at least one HNK-1 mimetic peptide (or a polypeptide comprising such HNK-1 mimetic peptide) may be administered prophylactically under clinical circumstances, where an infection with Pseudomonas is to be expected, for example, with immunocompromised patients, such as cancer patients undergoing chemotherapy. The composition may also be administered prophylactically to patients, which show an increased susceptibility for bacterial infections, in particular Pseudomonas infection. Such patients include, for example, patients with compromised respiratory tract functions, for example, patients suffering from cystic fibrose. Alternatively, the composition comprising at least one HNK-1 mimetic peptide (or a polypeptide comprising such HNK-1 mimetic peptide) may be administered to patients diagnosed with a Pseudomonas infection. A composition comprising at least one HNK-1 mimetic peptide may also be applied prophylactically to wounds or burned skin for protection against Pseudomonas infection.

In a particular preferred embodiment of the invention, the composition comprising at least one HNK-1 mimetic peptide is for use in the treatment or management of wounds, such as acute and chronic wounds. Chronic wounds are wounds which fail to heal within a time period commonly observed in normal wound healing (i.e. in patients with an unimpaired wound healing). Chronic wounds comprise, for example, diabetic leg or feet ulcers, pressure ulcers (decubitus ulcers) and arterial ulcers. Bacterial colonization of wounds regularly contributes to the non-healing state of chronic wounds. There is evidence that certain bacteria, such as bacteria of the genus Pseudomonas, are involved in biofilm formation within the wound which accounts for the failure of chronic wounds to heal. An early stage of Pseudomonas biofilm development is the association of bacterial cells with the wound surface which can be prevented by the mimetic peptides of the invention. Specifically, the peptides of the invention interfere with the capability of lectins of Pseudomonas to mediate adhesion of the bacteria to human cells, in particular epithelial cells and connective tissue, in the wound. Thus, the peptides of the invention are highly suitable for the treatment of wounds, and in particular chronic wounds, in order to prevent biofilm formation and promote accelerated wound healing. The HNK-1 mimetic peptides of the invention may be delivered to wounds by a route of administration that is commonly used in wound treatment, for example, in a composition for topical use, e.g. a solution, cream, ointment, salve or spray.

The HNK-1 mimetic peptides to be used according to the invention may be prepared by any suitable method for producing peptide molecules. Both ribosomal and non-ribosomal strategies are available in the art. Polypeptides with more than 50 amino acid residues are often prepared via recombinant expression systems using host organism, such as bacteria or yeast. A typical approach comprises culturing a host cell, such for example bacterial cells or yeast cells, containing a suitable expression vector comprising a nucleic acid sequence encoding the desired HNK-1 mimetic peptide, under conditions suitable for the expression of said peptide, and recovering said HNK-1 peptide from the cell culture.

The HNK-1 mimetic peptides of the invention may also be prepared recombinantly as fusion peptides or fusion polypeptides. As used herein, a fusion peptide or fusion polypeptide refers to a fusion of a first amino acid sequence comprising the HNK-mimetic peptide of interest which is N-terminally or C-terminally linked to a second amino acid sequence. The second amino acid sequence is usually an affinity tag, i.e. an amino acid sequence that is fused to the 5' or 3' end of the HNK-1 mimetic peptide and which exhibits an increased affinity to another compound, thereby allowing purification of the fusion protein. Preferably, the tag sequence is removed from the HNK-1 mimetic peptide of interest after purification, for example by providing a proteolytic cleavage site between the HNK-1 mimetic peptide and the affinity tag.

Smaller peptides are usually prepared by chemical synthesis. For example, the peptides may be chemically synthesized by solid phase or liquid phase methods. Protocols for solution-phase chemical synthesis of peptides have been described (see, for example, Andersson et al., Biopolymers 55:227-250, 2000). For solid phase synthesis the technique described by Merri-field (J. Am. Chem. Soc., 1964, 85, 2149-2154) may be used. In this approach, the growing peptide is anchored on an insoluble resin, and unreacted soluble reagents are removed by filtration or washing steps without manipulative losses. Solid phase peptide synthesis can be readily performed by use of automated devices.

The determination of amino acid identity or homology is well known in the art. Such determination may be performed, for example, by use of commercially available computer software, such as BLAST, FASTA, or SSEARCH operated with default parameters (see Altschul, et al., J. Mol. Biol., 215: 403-410 (1990); Altschul, et al., Nucl. Acids Res 25(17) 3389-3402 (1997); Pearson, W R., Methods in Enzymology 266:227-258 (1996); Henikoff and Henikoff, Proc Nat. Acad. Sci. 89:10915-10919 (1992)).

If homologs of the peptide molecules referred to in the sequence listing are used which exhibit 90% or more identity to a peptide from the sequence listing, it is preferred that the deviating amino acid residues are conservative amino acid substitutions. A conservative amino acid substitution is a substitution in which an amino acid residue is replaced with another residue having a chemically similar side chain. Families of amino acid residues having similar side chains have been defined in the art. These families include amino acids with acidic side chains (e.g., aspartic acid, glutamic acid), basic side chains (e.g., lysine, arginine, histidine), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The invention also contemplates the use of fragments of HNK-1 mimetic peptides, and in particular fragments of the peptides shown in SEQ ID NO:1-18. As used herein, a fragment of a peptide molecule means then when compared to the sequences depicted in the sequence listing, one or two of the amino acids at either end of the molecule might be missing provided, however, that the peptide molecule is still recognized by *Pseudomonas* lectins, such as PA-IL and PA-IIL of *Pseudomonas aeruginosa*.

The present invention provides pharmaceutical compositions useful for treating or preventing *Pseudomonas* infections. The preparation of pharmaceutical compositions containing a peptide as active ingredients is well known by those working in the field of pharmaceutics. Typically such compositions are prepared either as liquid solutions, powders or suspensions. Alternatively, the active ingredient may be emulsified in the compositions. The active ingredient can be mixed with excipients which are pharmaceutically acceptable and compatible with the active ingredient and in amounts suitable for use in the patients, such as humans.

In particular, the pharmaceutical compositions of the present invention may contain a physiologically acceptable carrier together with the mimetic peptides dissolved or dispersed therein as an active ingredient. As used herein, the term "pharmaceutically acceptable carrier" comprises, but is not limited to, water, saline, Ringer's Solutions, dextrose solution, and 5% human serum albumin. Liposome-based carriers and non-aqueous vehicles such as fixed oils may also be used. Further examples of suitable carriers for compositions comprising one or more HNK-1 mimetic peptides are described in standard textbooks, for example, in "Remington's Pharmaceutical Sciences", Mack Pub. Co., New Jersey (1991). In addition to the carrier, the composition may also contain further compounds, such as wetting agents, emulsifying agents, pH buffering agents, stabilizers, dyes and the like, insofar as these compounds do not interfere with the activity of the HNK-1 mimetic peptides on PA-IL and PA-IIL binding. According to a preferred embodiment of the invention, the pharmaceutical compositions of the present invention contain peptidic vectors for internalizing the HNK-1 mimetic peptide into the cells or tissues at the site where the therapeutic effect is desired. Suitable peptidic vectors are described, for example, in U.S. Pat. No. 6,080,724.

The pharmaceutical composition provided by the present invention will be formulated to be compatible with the intended route of administration. Different routes of administration are feasible for providing the HNK-1 mimetic peptides to the patient in need of treatment. The pharmaceutical composition may be formulated for parenteral administration, for example, for intravenous, intrathecal, intradermal, subcutaneous, topical, transmucosal, or rectal administration. Solutions or suspensions used for parenteral, intradermal or subcutaneous application usually comprise a sterile diluent such as water, saline solution, fixed oils, polyethylene glycols, glycerine, propylene glycol or other synthetic solvents. The solutions or suspensions may further comprise antibacterial agents such as benzyl alcohol or methyl parabens, antioxidants such as ascorbic acid or sodium bisulfite, chelating agents such as EDTA, buffers such as acetates, citrates or phosphates, and agents for the adjustment of tonicity such as sodium chloride or dextrose. The pH can be adjusted with suitable acids or bases, such as hydrochloric acid or sodium hydroxide. The parenteral preparation can be enclosed in ampoules, disposable syringes or multiple dose vials made of glass or plastic.

Pharmaceutical compositions suitable for injection normally include sterile aqueous solutions or dispersions and sterile powders for the extemporaneous preparation of sterile injectable solutions or dispersion. The composition intended for injection must be sterile and should be fluid in order to allow a convenient handling in a syringe. The composition should be stable under the conditions of manufacturing and storage and is preferably preserved against the contaminating action of microorganisms such as bacteria and fungi, for example, by including parabens, chlorobutanol, phenol, ascorbic acid, thimerosal, and the like into the composition. For intravenous administration, suitable carriers may comprise physiological saline, bacteriostatic water, Cremophor EL™ (BASF) or phosphate buffered saline (PBS). The carrier may also be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prolonged absorption of the injectable compositions can be achieved by including in the composition an agent which delays absorption, for example, aluminum monostearate or gelatin. Sterile injectable Solutions can be prepared by incorporating the active ingredient (the HNK-1 mimetic peptides) in the required amount in an appropriate solvent with one or a combination of the above mentioned ingredients followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable Solutions, methods of preparation are vacuum drying and freeze-drying that yields a powder of the active ingredient plus any additional desired ingredient from a previously sterile-filtered solution thereof.

The pharmaceutical composition according to the invention may be formulated for being administered by continuous infusion, for example, continuous infusion for a period of between 2 and 21 days, more preferably a period of between 10 and 14 days.

According to a particularly preferred embodiment, the pharmaceutical composition of the invention comprising the HNK-1 mimetic peptide (or the polypeptide comprising such HNK-1 mimetic peptide) is formulated for topical administration. This route of administration is preferred for the treatment of skin injuries, such as burns and wounds in order to prevent infection with *Pseudomonas aeruginosa*. In the context of the present invention, a topical administration refers to the application of the composition to the surface of the skin or mucosal tissue. Such administration includes the delivery of the composition to alveolar, buccal, lingual, masticatory, and nasal mucosa. The pharmaceutical composition of the invention may be present in the form of a solution, cream, ointment, salve or spray. Pharmaceutical compositions formulated for topical use may include, apart from the active peptides or polypeptides of the invention, suitable carriers and additives such as emollients, dyes, thickening or gelling agents, buffers and vitamins. Suitable carriers include cream or ointment bases or alcohol. Such carriers may be present as from about 1% up to about 98% of the formulation. The ointment base can comprise compounds like mineral oil, lanolin alcohol, panthenol, glycerin, cocoa butter and the like.

Administration of the mimetic peptides or polypeptides may also be achieved by transmucosal or transdermal delivery (Chen et al., Nature Biotechnology 24, 455-460 (2006). For transmucosal or transdermal administration, the pharmaceutical composition of the invention containing or HNK-1 mimetic peptides or polypeptides will comprise penetrants appropriate for the barrier to be permeated. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Preferably, the compounds are be prepared in the form of suppositories, with conventional suppository bases such as cocoa butter and other glycerides or retention enemas for rectal delivery.

According to a particularly preferred embodiment, the pharmaceutical composition of the present invention is formulated for administration by (oral or intranasal) inhalation. Such inhalation may be effected by pressurized metered dose inhalers, nebulizers and dry powder inhalers. According to a particularly preferred embodiment of the invention, the composition of the invention is formulated in the form of a presureized metered dose inhaler. In the metered dose inhaler, the active peptide(s) may be suspended or dissolved in a liquid propellant mixture. The propellants which can be used in a metered dose inhaler include chlorofluorocarbons (CFCs), hydrocarbons, or hydrofluorocarbons (HFAs). Preferred propellants according to the invention are HFA 134a (1,1,1,2-tetrafluoroethane), HFA 227 (1,1,1,2,3,3,3-heptafluoropropane) or mixtures thereof. The mixture comprising the active peptide(s) and the propellant are optionally used in combination with one or more additives such as co-solvents, surfactants, antioxidant, stabilizing or preserving agents.

In one embodiment, the active compounds are prepared with carriers that will protect the peptides against elimination from the body, such as a controlled release formulation, including implants and microencapsulated delivery Systems. Biodegradable, biocompatible polymers can be used, such as ethylene vinyl acetate, polyanhydrides, polyglycolic acid, collagen, polyorthoesters, and polylactic acid. Methods for preparing controlled release formulation are well-known in the art. Furthermore, sustained-release compositions can be prepared. Suitable examples of sustained-release preparations include semipermeable matrices of solid hydrophobic polymers, which matrices are in the form of shaped articles, e.g., films or microcapsules. Examples of sustained-release matrices include polyesters, hydrogels, polylactides, copolymers of L-glutamic acid and ethyl-L-glutamate, non-degradable ethylene-vinyl acetate, degradable lactic acid-glycolic acid copolymers and the like.

The therapeutic composition of the present invention can include pharmaceutically acceptable salts of the components therein. As used herein, pharmaceutically acceptable salts include acid addition salts (formed with the free amino groups of the polypeptide) that are formed with inorganic acids such as, for example, hydrochloric or phosphoric acids, or such organic acids as acetic acid or tartaric acid and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Particularly preferred are the salts of TFA and HCl, when used in the preparation of cyclic peptides.

The pharmaceutical compositions of the invention comprise at least one HNK-1 mimetic peptide in a therapeutically effective amount. As used herein, a therapeutically effective amount means that each peptide of the combination has to be present in an amount that is sufficient for effectively preventing a *Pseudomonas* infection as compared to a control which did not receive any HNK-1 mimetic peptide. Alternatively, a therapeutically effective amount may be an amount of peptide which is associated with an effective treatment of a disease caused by a *Pseudomonas* infection. An effective treatment may include alleviation of the signs, symptoms, or causes of a disease, or any other desired alteration of the patient's state of health. For example, if an infection of the respiratory tract is to be treated, an effective treatment will regularly comprise the reduction of the number or density of the microbial cells adhered to the mucosal surface, or an improvement in symptoms like coughing. Alternatively, the reduction of inflammatory marker molecules such as TNF-alpha may be measured to show effectiveness of the treatment.

A therapeutically effective amount of a HNK-1 mimetic peptide is typically an amount of peptide such that, when administered in a physiologically tolerable composition, is sufficient to achieve a plasma concentration in the patient from about 0.2 µg/ml to about 200 µg/ml, preferably from about 1 µg/ml to about 100 µg/ml, wherein 50 µg/ml is particularly preferred. Hence, the preferred plasma concentration of the HNK-1 mimetic peptide after administration will be in a range from about 0.005 mM to about 5 mM, and preferably about 0.5 mM to 2 mM, wherein a concentration of 1 mM is particularly preferred. Therefore, according to a preferred embodiment, the dosage per body weight can vary from about 0.15 mg per kg body weight of the patient to about 400 mg per kg body weight of the patient, and preferably from about 0.5 mg per kg body weight of the patient to about 200 mg per kg body weight of the patient, used in one or more dose administrations daily. Thus, according to a preferred embodiment of the invention, the therapeutically effective amount of the HNK-1 mimetic peptide ranges from 0.15 mg per kg body weight of the patient to about 400 mg per kg body weight of the patient.

It will be appreciated by those skilled in the art that the concrete amount of the HNK-1 mimetic peptide to be administered to the patient will depend on several factors, such as age and weight of the patient, as well as from the particular peptide combination and from the nature and severity of the medical symptoms to be treated. The amount will in any individual case may be determined by one of ordinary skill in the art using routine experimentation.

DESCRIPTION OF THE FIGURES

FIG. 4 shows the modulation of the CBF by PA lectins co-incubated with different concentrations of pHNK-1 and sHNK-1 over a 24 h period. The analysis showed a reduction of the CBF after addition of 10 μg/ml PA-IL (A and B). The co-incubation of 10 μg/ml PA-IL with 0.968 mM pHNK-1 (A), 0.484 mM pHNK-1 (A) and 0.968 mM sHNK-1 reduced the CBF-decreasing effect of the PA lectin. The addition of 10 μg/ml PA-IL to 0.242 mM pHNK-1 (A), 0.121 mM pHNK-1 (A), 0.484 mM sHNK-1 (B), 0.242 mM sHNK-1 (B) and 0.121 mM sHNK-1 (B) resulted in a continuous decrease of the CBF within 24 h. Furthermore, the analysis showed a decline of the CBF after addition of 10 μg/ml PA-IIL (C and D). The co-incubation of 10 μg/ml PA-IIL with 0.968 mM pHNK-1 (C) reduced the CBF-decreasing effect of the PA lectin. The addition of 10 μg/ml PA-IIL to 0.121-0.484 mM pHNK-1 (C) and 0.121-0.968 mM sHNK-1 (D) resulted in a continuous decrease of the CBF within 24 h. In addition, the simultaneous application of PA-IL and PA-IIL resulted in a decrease of the CBF, which could be inhibited by 0.968 mM pHNK-1 (E). The CBF of the negative control remained within the normal range (10-18 Hz). Values represent means±SEM.

EXAMPLES

The present invention will be further illustrated by the following examples. It should be understood that these examples are provided by way of illustration only, and are not intended to limit the scope of the invention.
Materials and Methods
Tissue Preparation Experiments were carried out on human nasal conchae, obtained during routine surgery from the ENT Hospital of the University Medical Center Hamburg-Eppendorf, Hamburg, Germany. For the measurement of CBF, small pieces of nasal mucosa were punched out of the nasal conchae by a special biopsy punch (Stiefel Laboratorium GmbH, Offenbach, Germany) (4-6 pieces per nasal conchae) and transferred to Petri dishes (Greiner Bio-One, Kremsmünster, Austria) containing RPMI-1640 and L-Glutamine medium (Gibco, Karlsruhe, Germany) supplemented with 10% fetal calf serum (Gibco, Karlsruhe, Germany), 1% Penicillin-Streptomycin (10 000 U/ml, Gibco, Karlsruhe, Germany) and 0.9% Amphotericin B (250 UG/ml, Gibco, Karlsruhe, Germany) as a fungicide. The specimens were maintained under standard cell culture conditions at 37° C. in 5% $CO_2$ for up to two weeks.
Measurement of CBF The aim of this experiment was to compare the efficiency of different sugar solutions and peptides to block PA-IL and PA-IIL binding to cilia in tissue sections and in vitro airway cultures by measuring their ciliary beat frequency (CBF). Actively beating ciliated cells were viewed trough phase-contrast optics of a Leica DM IRB HC inverted microscope (Leica, Bensheim, Germany) placed on a Micro-g vibration isolation table (TMC, Peabody, Mass.). During the experiments, the cultured tissue samples were maintained at a constant temperature (35±0.5° C.) by a thermostatically controlled heated stage. The signals were measured and analysed by a computer system incorporating a special purpose MPV-CBF software (Software-Entwicklung Radmann, Solms, Germany). The CBF was calculated by collecting data from 512 readings (10 s) and by performing Fourier analysis (Mewe et al. 2005). Five of these Fourier transforms taken per nasal conchae piece were measured.

The influence of monosaccharides and several peptides (obtained from Centre for Molecular Neurobiology, Hamburg, Germany) alone and in combination with PA-IL or PA-IIL on CBF was also investigated. The monosaccharides (0.2 M) and peptides (0.968 mM) were pre-incubated with 10 μg/ml PA-IL and 10 μg/ml PA-IIL, respectively, for 30 min at room temperature, at which they were agitated the for whole time and then added to the medium and the CBF was monitored over a 24 h period. Measurement was carried out after 0, 1, 2, 3, 5, 8, 24 h incubation. Negative controls were maintained in medium with no additions made. Positive controls were maintained in medium with PA-IL or PA-IIL, respectively.

Example 1

Inhibition of PA-IL Binding by Monosaccharides and Peptides

In CBF analysis, the influence of monosaccharides (D-galactose and L(−)-fucose) and the HNK-1 mimetic peptide pHNK-1 alone and in combination with PA-IL on CBF was investigated. Negative controls were within the normal range of between 10 and 18 Hz (FIG. 1). The monosaccharides (FIG. 1A) and peptides (FIGS. 1B and 1C) alone had no effect on CBF. The addition of 10 μg/ml PA-IL caused a decrease of CBF within 24 hours. The CBF-decreasing effect of PA-IL could be effectively reduced when the lectin was co-incubated with 0.2 M D-galactose (FIG. 2A). However, 0.2 M L(−)-fucose did not inhibit the PA-IL induced suppression of ciliary beat within 24 hours (FIG. 2A).

Furthermore, the CBF-decreasing effect of PA-IL could be reduced when PA-IL was co-incubated with peptides pHNK-1 (FIG. 2B) at a concentration of 0.968 mM, while peptides mimicking pLeX (FIG. 2C) did not have any significant effects on CBF. Unexpectedly, the scrambled version of the peptide pHNK-1 also reduced the CBF-decreasing effect of PA-IL, while the control peptide pLeX had no effect.

Example 2

Inhibition of PA-IIL Binding by Monosaccharides and Peptides

Figure 2:
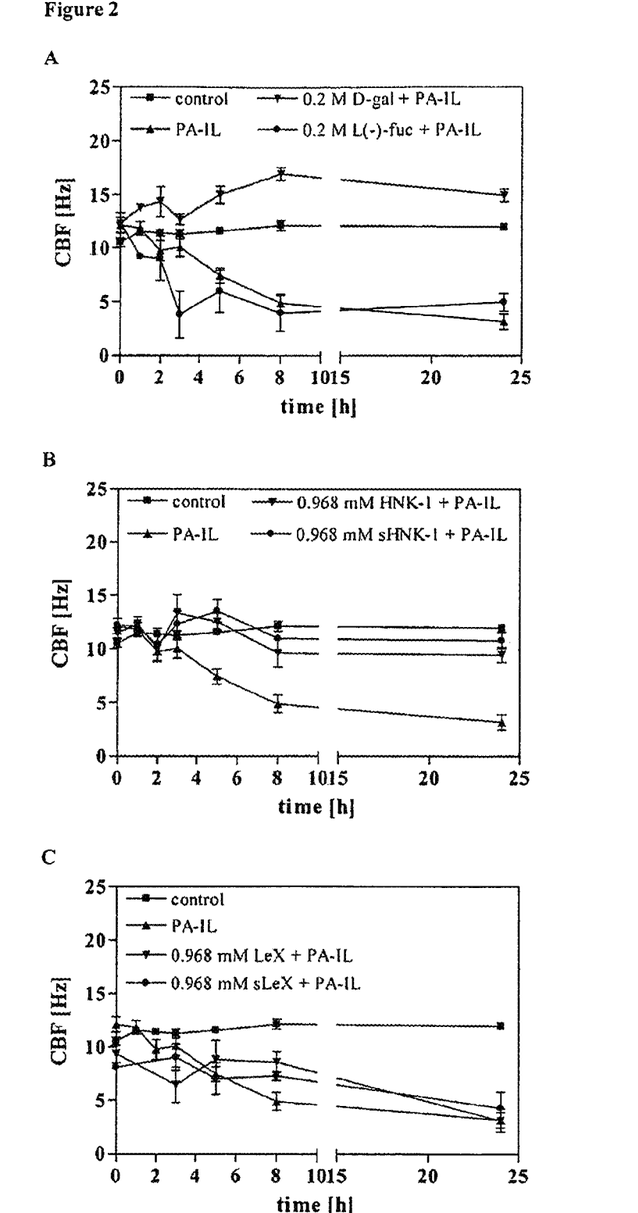
FIG. 2 shows the modulation of the CBF by PA-IL co-incubated with monosaccharides and glycomimetic peptides over a 24 h period. The analysis showed a decrease of the CBF after the addition of 10 μg/ml PA-IL. The co-incubation of 10 μg/ml PA-IL with 0.2 M D-galactose (A), 0.968 mM pHNK-1 (B), and 0.968 mM sHNK-1 (B) reduced the CBF-decreasing effect of the PA lectin. The addition of 10 μg/ml PA-IL to 0.2 M L(−)-fucose (A) or 0.968 mM pLeX (C) resulted in a continuous decrease of the CBF within 24 h. The CBF of the negative control remained within the normal range (10-18 Hz). Values represent means±SEM.
Figure 3:
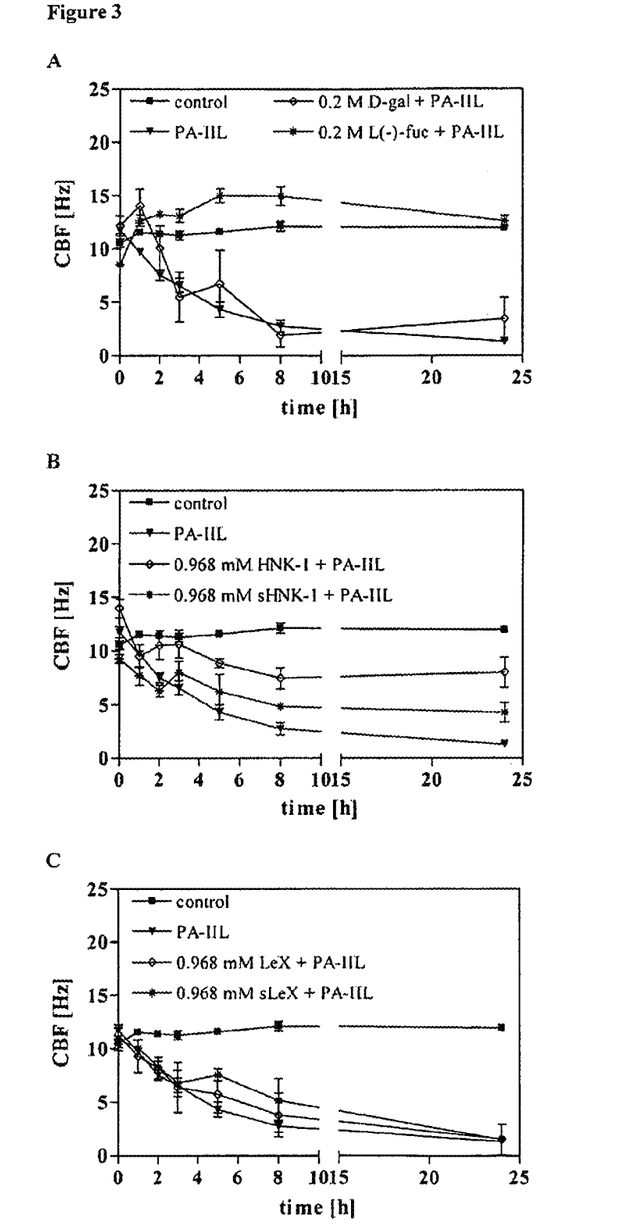
FIG. 3 shows the modulation of the CBF by PA-IIL co-incubated with monosaccharides and glycomimetic peptides over a 24 h period. The analysis showed a decrease of the CBF after addition of 10 μg/ml PA-IIL. The co-incubation of 10 μg/ml PA-IIL with 0.2 M L(−)-fucose (A) and 0.968 mM pHNK-1 (B) reduced the CBF-decreasing effect of the PA lectin. The addition of PA-IIL to 0.2 M D-galactose (A) and the glycomimetic peptide pLeX (C) resulted in a decline of the CBF within 24 h. The CBF of the negative control remained within the normal range (10-18 Hz). Values represent means±SEM.

For CBF analysis monosaccharides (D-galactose and L(−)-fucose) and peptides were pre-incubated with PA-IIL and the CBF was determined. Negative controls were within the normal range of between 10 and 18 Hz (FIG. 3). The addition of 10 μg/ml PA-IIL resulted in a decrease of the CBF within 24 hours, and this decrease in CBF was considerably more intensive than the one observed with PA-IL (FIG. 2). The CBF decreasing effect of PA-IIL was reduced when the PA-IIL was co-incubated with 0.2 M L(−)-fucose (FIG. 3A). However, 0.2 M D-galactose did not inhibit the PA-IIL induced decrease of ciliary beat within 24 hours (FIG. 3A).

In addition to fucose, the CBF-decreasing effect of PA-IIL could only be blocked when PA-IIL was co-incubated with 0.968 mM pHNK-1 peptide (FIG. 3B), while none of the other tested peptides (sHNK-1, pLeX, sLeX) had any consequence for CBF-decreasing effect of PA-IIL (FIGS. 3B and 3C).

Example 3

Inhibition of PA-IL and PA-IIL Binding by pHNK-1 and sHNK-1

Figure 4:
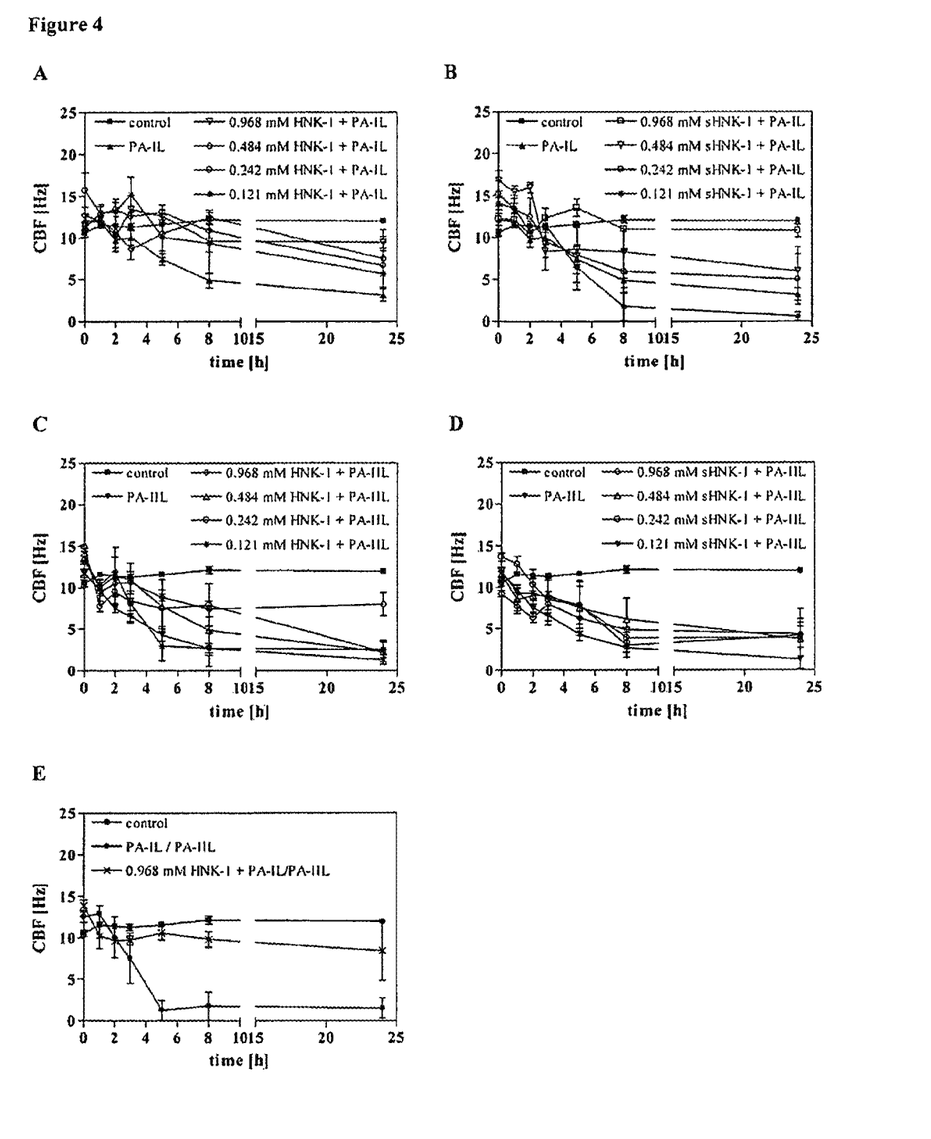

As pHNK-1 inhibited both lectins, the blocking activity of this peptide was further investigated. Different concentrations (0.968 mM, 0.484 mM, 0.242 mM, 0.121 mM) of pHNK-1 and its control peptide sHNK-1 were prepared, co-incubated with PA-IL and PA-IIL, the CBF was investigated and $IC_{50}$ values were determined. The addition of PA-IL to the human airway cilia caused a decrease of the CBF after 24 hours and could be inhibited by both pHNK-1 ($IC_{50}$ 0.484 mM) (FIG. 4A) and sHNK-1 ($IC_{50}$ 0.968 mM) (FIG. 4B). The application of PA-IIL also resulted in a continuous decline of the CBF and could be reduced when the lectin was co-incubated with pHNK-1 ($IC_{50}$ 0.968 mM) (FIG. 4C), while sHNK-1 had no effect. The simultaneous addition of PA-IL and PA-IIL resulted in a sharp decrease of CBF which reached its minimum already after five hours of incubation. Interestingly, however, the decline was significantly stronger than that observed for PA-IL or PA-IIL alone. The binding of both lectins to the human airway cilia could be inhibited by 0.968 mM pHNK-1 (FIG. 4E). Consequently, pHNK-1 acts as a specific inhibitor for both PA-IL and PA-IIL.

The invention claimed is:

1. A method for treating a *Pseudomonas* infection comprising administering to a patient an effective amount of a pharmaceutical composition comprising a HNK-1 mimetic peptide or a polypeptide comprising such HNK-1 mimetic peptide, wherein the HNK-1 mimetic peptide comprises Phe-Leu-His-Thr-Arg-Leu (SEQ ID NO:21).

2. The method according to claim 1, wherein said HNK-1 mimetic peptide comprises or consists of an amino acid sequence selected from the group of amino acid sequences depicted in SEQ ID NO:1, SEQ ID NO:2, SEQ ID NO:4, SEQ ID NO:5, SEQ ID NO:6, SEQ ID NO:7 or SEQ ID NO:8.

3. The method according to claim 2, wherein said HNK-1 mimetic peptide comprises or consists of the amino acid sequence depicted in SEQ ID NO:1.

4. The method according to claim 1, wherein the *Pseudomonas* infection is caused by *Pseudomonas aeruginosa*.

5. The method according to claim 1, wherein the patient is suffering from cystic fibrose or wounds.

6. The method according to claim 1, wherein the composition is for administration by inhalation.

7. The method according to claim 6, wherein the composition is for administration in a metered dose inhaler.

* * * * *